(12) United States Patent
Heidari

(10) Patent No.: US 7,928,392 B1
(45) Date of Patent: Apr. 19, 2011

(54) SYSTEMS AND METHODS FOR BLIND ECHO CANCELLATION

(75) Inventor: Abdorreza Heidari, Kitchener (CA)

(73) Assignee: T-Ray Science Inc., Waterloo, Ontario ( * ) Notice: Subject to any disclaimer, the term of this patent is extended or adjusted under 35 U.S.C. 154(b) by 10 days.

(21) Appl. No.: 12/575,184

(22) Filed: Oct. 7, 2009

(51) Int. Cl.
*G01N 21/17* (2006.01)

(52) U.S. Cl. .................................................... 250/340

(58) Field of Classification Search .................. 250/340, 250/341.1; 370/286; 379/406.8
See application file for complete search history.

(56) References Cited

U.S. PATENT DOCUMENTS

| | | | |
|---|---|---|---|
| 4,813,073 A | 3/1989 | Ling | |
| 5,414,766 A | 5/1995 | Cannalire et al. | |
| 5,623,145 A | 4/1997 | Nuss | |
| 5,909,426 A | 6/1999 | Liau et al. | |
| 5,939,721 A | 8/1999 | Jacobsen et al. | |
| 6,317,419 B1 | 11/2001 | Olafsson et al. | |
| 6,526,141 B2 | 2/2003 | Benesty et al. | |
| 6,678,254 B1 | 1/2004 | Song | |
| 6,766,021 B2 | 7/2004 | Kurtz et al. | |
| 6,816,204 B2 | 11/2004 | Limberg | |
| 6,996,229 B2 | 2/2006 | Gunther | |
| 7,099,822 B2 | 8/2006 | Zangi | |
| 7,162,420 B2 | 1/2007 | Zangi et al. | |
| 7,362,791 B2 | 4/2008 | Tellado et al. | |
| 7,386,135 B2 | 6/2008 | Fan | |
| 7,400,693 B2 | 7/2008 | Langberg et al. | |
| 7,618,465 B2 * | 11/2009 | Klein et al. | 850/32 |
| 2002/0191779 A1 | 12/2002 | Pham | |
| 2007/0138392 A1* | 6/2007 | Cole | 250/341.1 |
| 2008/0309577 A1* | 12/2008 | Mittleman et al. | 343/850 |

* cited by examiner

*Primary Examiner* — David P Porta
*Assistant Examiner* — Marcus H Taningco
(74) *Attorney, Agent, or Firm* — Bereskin & Parr LLP/S.E.N.C.R.L., s.r.l.

(57) ABSTRACT

System and method for blind echo cancellation in a received terahertz signal in a pulsed terahertz system for imaging or spectroscopy. Blind signal processing methods estimate the impulse response of the reflection mechanism and do not require a reference measurement to be taken. The reference signal may be recovered using a successive approach wherein the reference is first estimated using cross-correlation with the received signal and the received signal is represented as a function of the reference signal. For each successive echo, the calculated echo may be subtracted from the received signal and then the estimate of the reference signal is refined. Using an analytical approach, the parameters of a transfer function modeling the reflection mechanism may be estimated by optimizing a cost function.

17 Claims, 8 Drawing Sheets

SYSTEMS AND METHODS FOR BLIND ECHO CANCELLATION

FIELD

The present invention relates to terahertz spectroscopy and imaging systems, and in particular, to systems and methods for processing terahertz signals to reduce the effect of echoes.

BACKGROUND

Terahertz radiation is electromagnetic waves that have a frequency between 100 GHz and 30 THz, lying between the infrared and microwave parts of the spectrum. The radiation is non-ionizing and can penetrate most non-metallic objects but is absorbed by polar materials and liquids. Consequently, terahertz technology provides a number of spectroscopy and imaging applications, and is a fast-growing field.

Terahertz pulses are distorted by passing though various materials including gases, liquids, and solids. It is well known that different materials alter the terahertz waves differently, depending on the material and the frequency content of the signal. It is the purpose of terahertz signal processing to detect and classify these changes. Depending on the application, some of the changes are undesired and must be compensated for.

In terahertz signal processing a detected signal often contains several echoes of the same signal due to reflections of the signal. Depending on the setup, reflections can come from sample edges, wave-guide ends, the terahertz source structure, the terahertz detector structure or any of a number of other sources. In some cases, multiple reflection mechanisms may be combined.

The simplest way to handle the reflection mechanisms in terahertz signal processing is to time-gate the signal before the occurrence of any echoes due to the reflections. However, by time-gating the signal, the frequency resolution of the signal is also decreased since it is inversely proportional to the time-length of the signal. Reduced frequency resolution results in a decreased image resolution in imaging applications, and in spectroscopy applications, may result in failing to detect spectroscopic indicators with a narrow frequency response.

Other approaches to minimize the echo effect have attempted to solve the problem with the hardware setup. However, due to the inherent nature of terahertz systems this approach is practically impossible, or at the least, costly in terms of the system complexity and terahertz signal quality.

Presently, the most practical solution involves taking an extra reference measurement without the sample to be measured present. The reference measurement is then differentiated or deconvolved from the main measurement to remove the reflection effects. However, in practice this may not be possible or easily accomplished. For example, if the reflection is coming from the sample to be measured, one could remove the sample and replace it with another object which generates exactly the same reflection effect. In spectroscopy, where the sample is unknown, or in cases where the sample is structurally complex, it is either impossible or very difficult to replace the sample without introducing other effects. Taking an extra reference measurement also does not account for the reflections within the structures of the terahertz emitter and detectors themselves. Also, temperature fluctuations, change in beam position, or other factors affecting laser stability between the reference measurement and sample measurement can introduce errors.

Accordingly, there is a need for improved signal processing in terahertz spectroscopy and imaging applications that can remove the echo effects without using a measured reference signal.

SUMMARY OF THE INVENTION

The present invention provides systems and methods of removing the adverse effect of reflections in a received terahertz signal without using a measured reference signal. The removal of the echo effect from the reflections without the use of a measured reference signal may be referred to as blind echo cancellation. The use of blind echo cancellations methods may be applied in applications where taking a measured reference signal is either impractical or may be inaccurate. Using blind echo cancellation methods also allows a larger time period of the signal to be analyzed, which in turn also allows a higher frequency resolution of the signal to be analyzed. This signal processing approach is beneficial in many applications, including imaging and spectroscopy applications.

According to a first aspect of the invention, there is provided a method for canceling echoes in a terahertz signal comprising the steps of receiving a terahertz signal containing echoes; estimating a reference signal from the received signal; calculating the echoes as a function of the reference signal; and for at least one of the successive echoes, subtracting the calculated echo from the received signal to form a refined reference signal; and re-calculating the echoes as a function of the refined reference signal.

The step of calculating the echoes and re-calculating the echoes comprises estimating the time-shift and amplitude of each of the echoes as a function of the corresponding reference signal. The step of subtracting the calculated echo may be repeated until a threshold is reached. The threshold may include defining the refined reference signal over a defined portion of the echo period; the number of recalculation iterations performed; the difference between the refined reference signal and the prior calculation of the refined reference signal.

The received signal may be expressed as a sum of scaled, time-shifted reference signals. The reference signal may also be estimated using cross-correlation with the received terahertz signal.

According to another aspect of the invention, there is provided a method for canceling echoes in a terahertz signal comprising the steps of receiving a terahertz signal containing echoes; calculating a reference signal as a function of the received signal; and estimating system parameters of a reflection mechanism by minimizing the energy of the reference signal. The system parameters may then be used in an inverse transfer function that may be used in a deconvolution with the received signal to remove at least one of the echoes.

According to another aspect of the invention, there is provided a system for canceling echoes in a terahertz signal, the system comprising a terahertz signal receiver for receiving a terahertz signal containing echoes; an estimator for estimating a reference signal from the received signal; an echo subtracter for subtracting an echo from the received signal to form a refined reference signal; and a signal calculator for calculating the echoes as a function of the reference signal, and for calculating the echoes as a function of the refined reference signal.

The reference signal may be modeled as a function of the received signal and the system parameters, wherein an attenuated and time-shifted received signal is subtracted from the received signal to remove the effects of the echo. The transfer function used to model the terahertz transmission may be based on a single slab medium in a vacuum.

BRIEF DESCRIPTION OF THE DRAWINGS

A preferred embodiment of the present invention will now be described in detail with reference to the drawings, in which.

DETAILED DESCRIPTION

Figure 1:
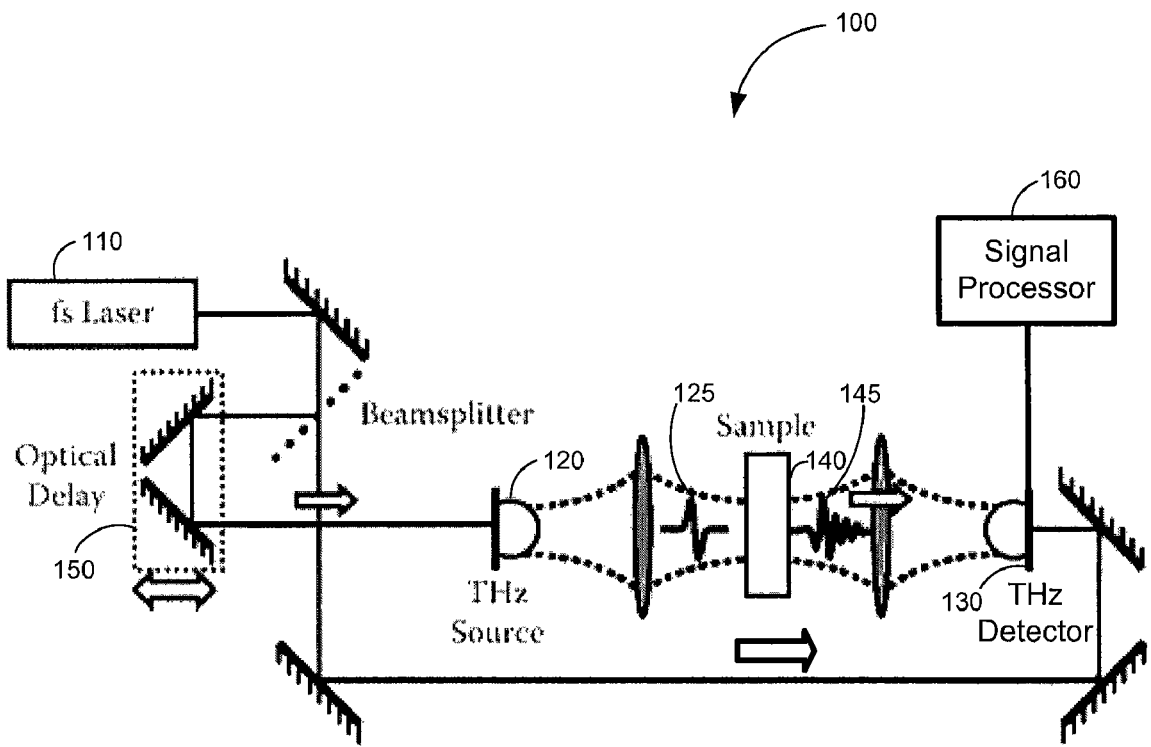
FIG. 1 is a schematic diagram of a terahertz radiation transmission and detection system made in accordance with an exemplary embodiment of the present invention.

Referring to FIG. 1, illustrated therein is a terahertz radiation transmission and detection system 100 made in accordance with an exemplary embodiment of the invention. The terahertz radiation system 100 may be used for either spectroscopy or imaging. The system 100 comprises a laser source 110 that is capable of generating optical pulses of femtosecond duration. The laser pulse excites the terahertz transmitter 120 to generate terahertz radiation 125 that may be directed at a sample 140 that is being analyzed. The sample 140 could be a gas, liquid or solid. The transmitted and reflected terahertz radiation 145 may then be received by the terahertz detector 130. The terahertz radiation at the detector 130 may then be measured as an electric current by a signal processor 160.

The laser source 110 is also used to excite the detector for the duration of the femtosecond pulse. An optical delay 150 may be used to create a relative delay between the pulse exciting the transmitter 120 and the detector 130. By adjusting the optical delay, the signal processor 160 is able to reconstruct the terahertz pulse shape.

The signal processor 160 may be a Digital Signal Processor; a custom integrated circuit or FPGA; a general purpose microprocessor; or a combination thereof. In some embodiments, the signal processor 160 may also comprise the analog-to-digital conversion components, or in other embodiments, the ND conversion could be a separate component connecting the detector with the signal processor. The signal processor 160 should have modules or be configured to reconstruct the terahertz signal in the time domain, a module to estimate the echo patterns using correlation or error calculations, and processing logic to coordinate the echo removal methods and process the received signal.

Figure 2:
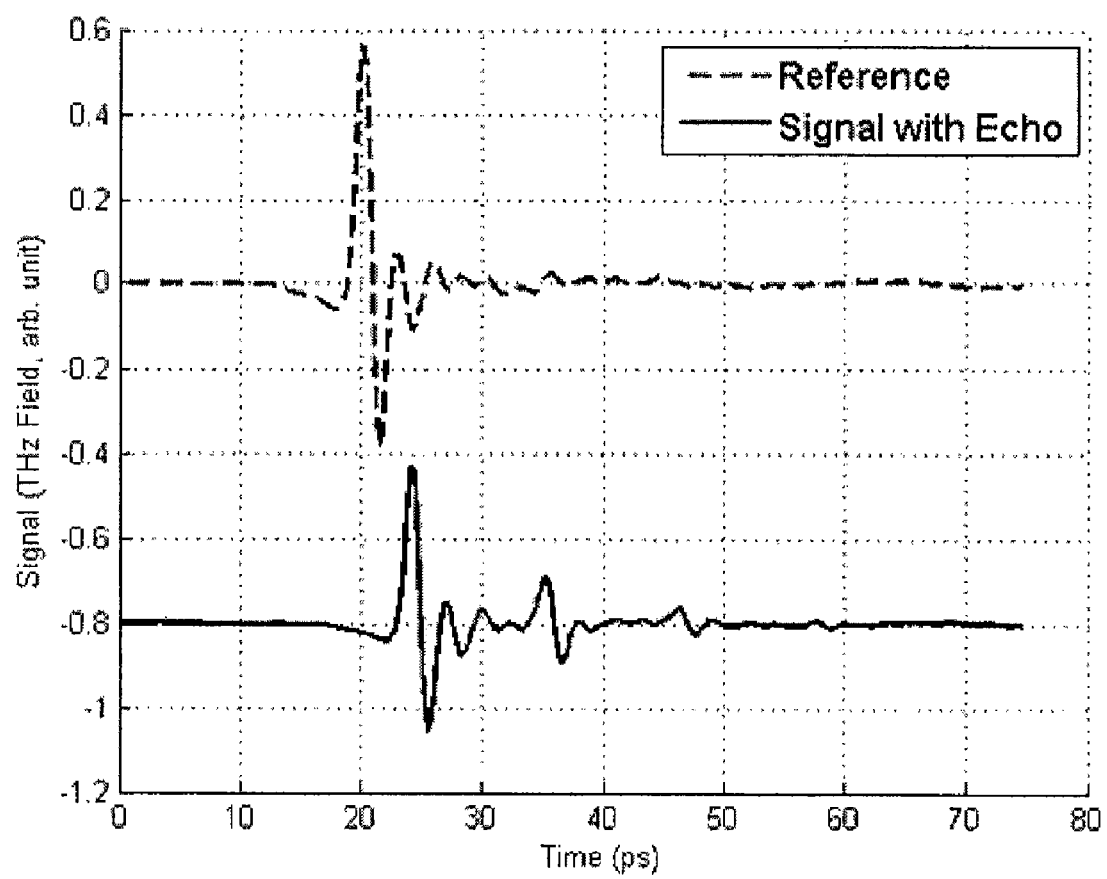
FIG. 2 is a graph representing the reference pulse and the reflected pulse with echoes.

FIG. 2 illustrates the terahertz wave generated by the terahertz transmitter 120 as received by the detector 130 with and without the sample present. The reference pulse is shown as the dashed line in FIG. 2 and is the result of a reference measurement taken without the sample present. With the sample present, the main measurement, shown as the solid line, shows the reflected pulse and contains echoes. Signal processing approaches that utilize a reference measurement may then differentiate (or deconvolve) the reference measurement from the main measurement to remove the reflection effects.

Figure 3A:
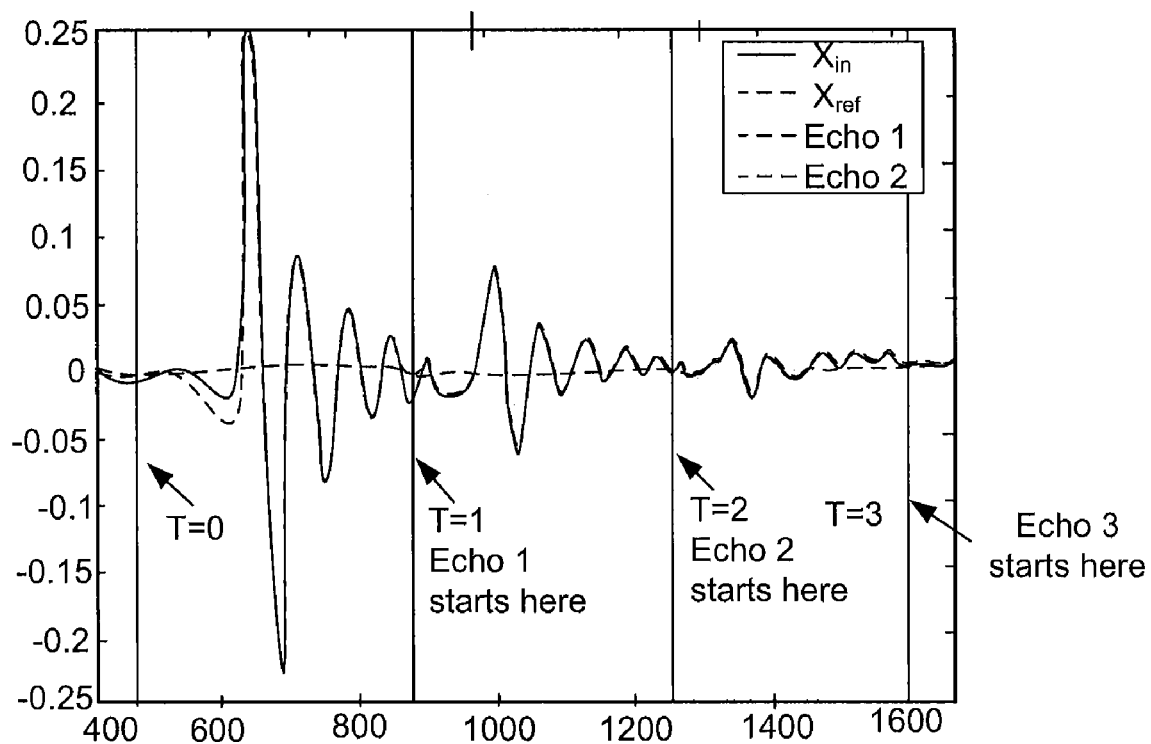
FIG. 3A is a waveform diagram of the received signal showing first and second order echoes.

FIG. 3A illustrates a signal received by the terahertz detector showing echoes that are relatively spaced apart. The received signal is a solid line noted as $X_{1n}$ and may be represented as a time-shifted sum of the reference signal and the echoes, each of which is indicated by dashed lines in FIG. 3A. The time period of each of the echoes is indicated in FIG. 3A with Echo 1 beginning at time T=1, Echo 2 beginning at time T=2, and Echo 3 beginning at time T=3.

Figure 3B:
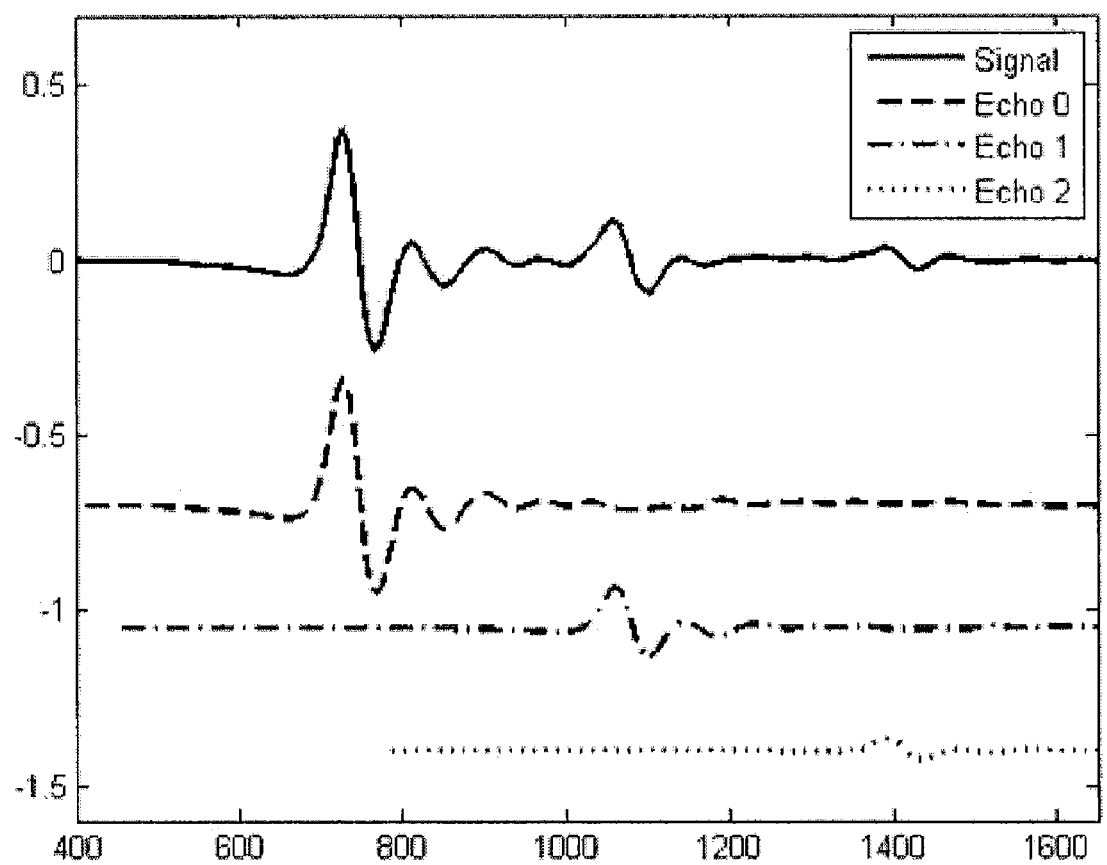
FIG. 3B is a waveform diagram of the received signal showing the individual echoes that compose the received signal.

FIG. 3B illustrates the received signal and each of the portions of the received signal from FIG. 3A. The received signal is composed of the signals: Echo 0 (or the reference signal), Echo 1 and Echo 2 shown in FIG. 3B.

The reflection mechanism may be modeled as an input-output system, where the input is the desired (reference) signal, and the output is the signal with echoes. Without considering the material dispersion of the sample, the system impulse response can be shown as:

$$h_s(t) = \sum_{p=0}^{N_p} \alpha_p \delta(t - \tau_p)$$

where $\delta(t)$ is the unit impulse function. This means that the output signal may be modeled as:

$$x_s(t) = \sum_{p=0}^{N_p} \alpha_p x_{ref}(t - \tau_p)$$

wherein $\alpha_p$ represents an attenuation of the reference signal and $\tau_p$ represents a time-shift of the reference signal.

Using the above model, the reference signal $x_{ref}(t)$ may then be recovered from the received signal $x_s(t)$ without a reference measurement. Referring again to FIG. 3, the received signal between the interval of $T_0$ and $T_1$ may be represented as follows:

$$x_s(t) = \alpha_0 x_{ref}(t-\tau_o) + \alpha_1 x_{ref}(t-\tau_1)$$

Therefore, part of the reference signal related to this time interval may be recovered from the received signal. In the next interval between $T_1$ and $T_2$, the received signal contains the first echo, shown as Echo1 in FIG. 3, and a further portion of the reference signal. The received signal over this interval may be represented as follows:

$$x_s(t) = \alpha_0 x_{ref}(t-\tau_o) + \alpha_1 x_{ref}(t-\tau_1)$$

Using an initial estimate of the reference signal based on the interval between $T_0$ and $T_1$, the echo portion of the signal may then be subtracted from the received signal within the interval from $T_1$ and $T_2$ to further refine the estimate of the reference signal. The refined estimate of the reference signal will now include a portion of the signal, between $T_1$ and $T_2$, that was obscured by the effects of Echo1.

Due to dispersion and other effects, the time period of the echoes may be longer than the time period of the initial estimate of the time period of the reference signal (i.e. $T_2-T_1 > T_1-T_0$). Therefore, removal of the echo using the time-limited reference signal may not completely cover the echo period. If the echo period is not completely covered, the later portion of the echo may continued to be removed from the received signal because now a larger portion of $x_{ref}(t)$ is known. This is similar to the first removal step as explained above. After each iteration of echo removal, the removal of Echo1 approaches $T_2$, therefore the period of the refined reference signal also approaches $T_2$.

For successive echoes, the echo removal process is similar to that shown for Echo1 above. Because t−tau1>t−tau2> . . . for any t, Echo1 has the strongest overlap with the reference signal. This means that Echo 1 is the limiting echo because it obscures the most energy of the reference signal.

Figure 4:
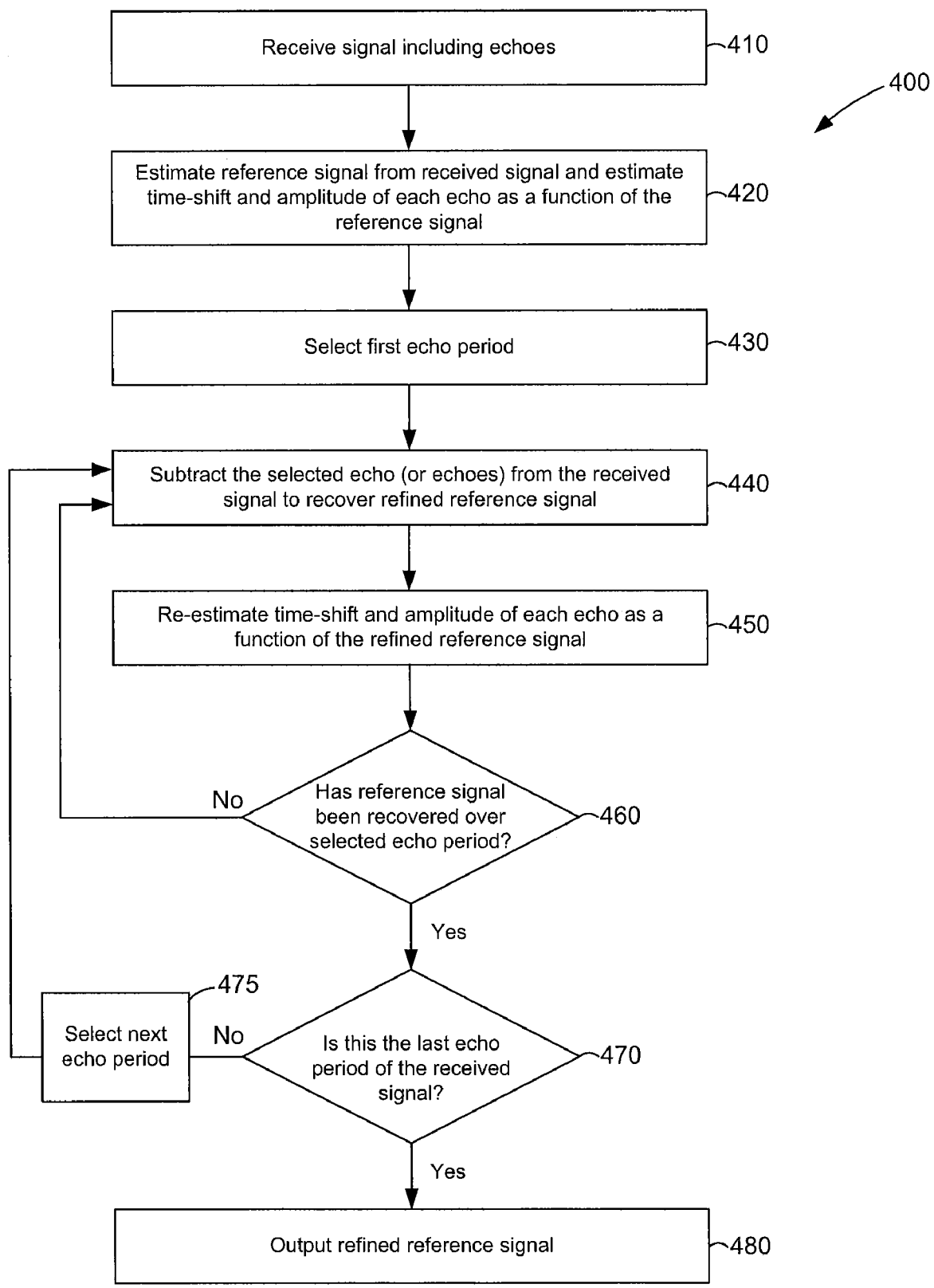
FIG. 4 is a flow chart of an embodiment of the successive blind echo cancellation method.

Now referring to FIG. 4, shown is a flowchart of an embodiment of a successive blind echo cancellation method 400. This method may be used to process signals received from a terahertz detector, such as that shown in FIG. 1. In step 410, an input signal is received that includes echoes. The input signal may be reconstructed from the received signals at the terahertz detector to obtain a time-domain representation of the electric current at the detector.

In the next step 420, an initial estimate of the reference signal may be obtained from the received signal. An autocorrelation approach may be used to estimate the reference signal and estimate the time-shift of each of the echoes. Once the initial estimate of the reference signal is obtained, the echoes may be represented as a function of the reference signal. Other correlation approaches may be applied using algorithms such as those taught by AV Oppenheim, RW Schafer, "Discrete-time Signal Processing", 1999-Prentice-Hall, Inc. As described above, the received signal may be modeled as the following sum:

$$x_s(t) = \sum_{p=0}^{N_p} \alpha_p x_{ref}(t - \tau_p)$$

wherein $\alpha_p$ represents an attenuation factor of the reference signal and $\tau_p$ represents a time-shift of the reference signal.

Next, in step 430, the first echo period is selected. The selected echo, as represented as a function of the reference signal, is then subtracted from the received signal to recover a refined reference signal in step 440. The refined reference signal will have a longer time period, since it now includes the portion that was obscured by the echo.

In step 450, the refined reference signal may now be used to re-estimate the time-shift and amplitude of each echo as a function of the refined reference signal. A cross-correlation approach may be used to correlate the refined reference signal with the received signal. In step 460 a determination is made whether the estimated reference signal has been recovered over the selected echo period. This step accounts for situations where the period of the selected echo is longer than that of the estimated reference signal such that the refined reference signal is not defined over the entire period of the selected echo. If this is the case, using the refined reference signal and the estimates of the time-shift and amplitude obtained in step 450, then step 440 is repeated to obtain a further refined reference signal. As this procedure goes on, a larger portion (and ideally a more accurate estimate) of the refined reference signal is recovered. The determination in step 460 may also be based on other factors, for example, the number of iterations performed, the amount of difference from the last refined reference signal, or the refined reference signal being recovered over a defined percentage of the selected echo period.

If the determination in step 460 is made in the affirmative, the process may then proceed to step 470 to determine if additional echo periods should be processed. In the embodiment shown in FIG. 4, this determination may be based on whether all of the echo periods of the received signal have been processed.

If additional echoes are to be processed, the next echo period may be selected in step 475. The estimates of the time-shift and amplitude of the echoes obtained in step 450 are used and the currently selected echo, along with the preceding echoes, are subtracted from the received signal to obtain a further refined reference signal.

In some embodiments, the step 470 may not be necessary as the system may be able to obtain a fairly accurate estimate of the reference signal without processing the additional echoes. In other embodiments, the determination in step 470 may be based on processing a certain number of echo periods or stopping when the calculation of the last refined reference signal does not significantly differ from the current calculation of the refined reference signal.

Finally, in step 480, the refined reference signal may be available for analysis or further signal processing. With the echoes removed from the signal a greater length of time of the signal may be analyzed. This in turn also increases the frequency resolution of the signal as it is inversely proportional to the time-length of the signal.

Another way to recover the reference signal is to estimate the impulse response of the terahertz system and then deconvolving this with the received signal in the time or frequency domain to recover the reference signal. This approach may be referred to as an analytical blind echo cancellation approach. Modeling the sample as a single slab medium in a vacuum, we can represent the Z-transform of the transfer function as follows:

$$h_S(Z) = \frac{\alpha Z^{-d}}{1 - \beta Z^{-2d}} \text{ where}$$

$$\alpha = \frac{4n}{(n+1)^2}, \beta = \left(\frac{n-1}{n+1}\right)^2, \text{ and } d = \frac{nL}{C} f_{samp}$$

where n and L are the refractive index and thickness of the slab, respectively, and $f_{samp}$ is the sampling frequency. This transfer function models most of the reflection mechanisms present in a terahertz system. Other embodiments of the invention may use alternative transfer functions that provide a model for other effects, including other reflection mechanisms, dispersion or other transmission effects.

Figure 5:
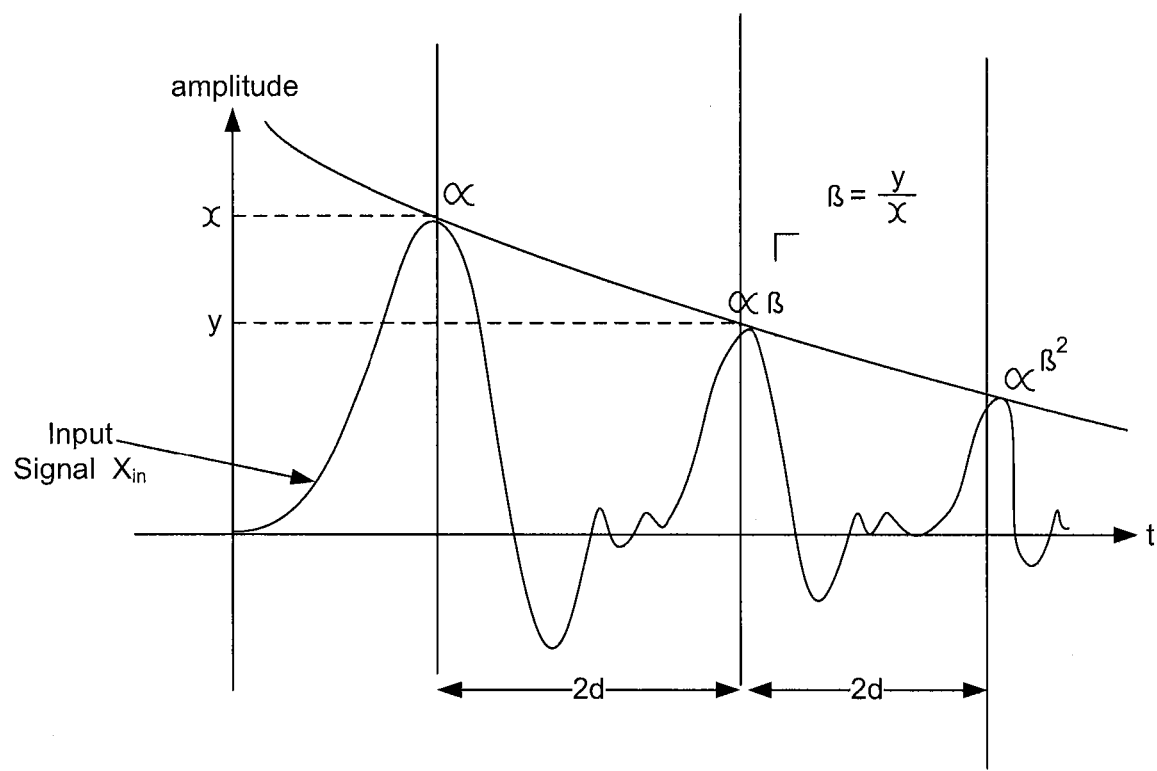
FIG. 5 shows a received terahertz signal with echoes modeled according to the slab model.

Most of the reflection mechanisms found in terahertz systems may be modeled as above. The model may be considered a first-order reflection mechanism. Now referring to FIG. 5, shown is a received terahertz signal with echoes according to the slab model. According to the first-order reflection mechanism, the power of the $n^{th}$ echo may be represented as $\alpha\beta^n$. Also, shown in FIG. 5, the length of the echoes are represented by distance $2d$.

If the reflection system in the terahertz system may be modeled by the transfer function $h_S(Z)$, as shown above, then the inverse of this transfer function may be used to recover the reference pulse. The following transfer function is the inverse of $h_S(Z)$:

$$g_S(Z) = 1 - \beta Z^{-2d}.$$

Since the gain and the time-shift are known, they may be incorporated into the result if necessary. Then, an estimate of the reference signal may be recovered through the following convolution with the Z-transform of the received signal:

$$\tilde{x}_{ref}(Z) = g_S(Z) x_S(Z)$$

where $\tilde{x}_{ref}(Z)$ represents the result of applying the inverse filter on the signal. Therefore, in the time domain, $\tilde{x}_{ref}(t)=\alpha x_{ref}(t-d)$.

Assuming that the analytical BEC algorithm applies, the reference signal may be calculated as follows:

$$\hat{g}_s(Z) = 1 - \hat{\beta} Z^{-2\hat{d}}$$

then, $$\hat{x}_{ref}(Z) = \alpha Z^{-\hat{d}} \left( \frac{1 - \hat{\beta} Z^{-2\hat{d}}}{1 - \beta Z^{-2d}} \right) x_{ref}(Z)$$

In the ideal case, $\hat{d}=d$ and $\hat{\beta}=\beta$, such that $\hat{x}_{ref}(Z)$ may be represented as the $x_{ref}(Z)$ pulse with a gain and a time-shift. However, if $\hat{d} \neq d$ or $\hat{\beta} \neq \beta$, there will be some remaining echoes in $\tilde{x}_{ref}(Z)$ after the main pulse.

To find the optimal values of $\hat{d}$ and $\hat{\beta}$ in a blind fashion, a cost function may be used in the following form:

$$J(\hat{d},\hat{\beta})=f(\hat{x}_{ref}(t)).$$

For example, some embodiments of the invention may use the energy of $\hat{x}_{ref}(t)$ as the cost function, namely $J(\hat{d}, \hat{\beta})=\|\hat{x}_{ref}(t)\|^2$. The function $\hat{x}_{ref}(t)$ may be estimated as a function of the received signal less a scaled, time-shifted copy of the received signal as follows:

$$\hat{x}_{ref}(t)=X_{in}-\hat{\beta} X_{in}(t-2\hat{d}).$$

This estimate takes into account only the first echo, but other embodiments may use more sophisticated functions to cancel the effect of the other echoes. In most cases, canceling the subsequent echoes may only provide marginal improvement in the signal quality. Next, in order to find the best calculation of the reference signal, the following optimization problem may be solved to find the optimal values $\hat{d}$ and $\hat{\beta}$:

$$\min_{\hat{d},\hat{\beta}} J(\hat{d}, \hat{\beta}) = \min_{\hat{d},\hat{\beta}} \|\hat{x}_{ref}(t)\|^2.$$

Figure 6:
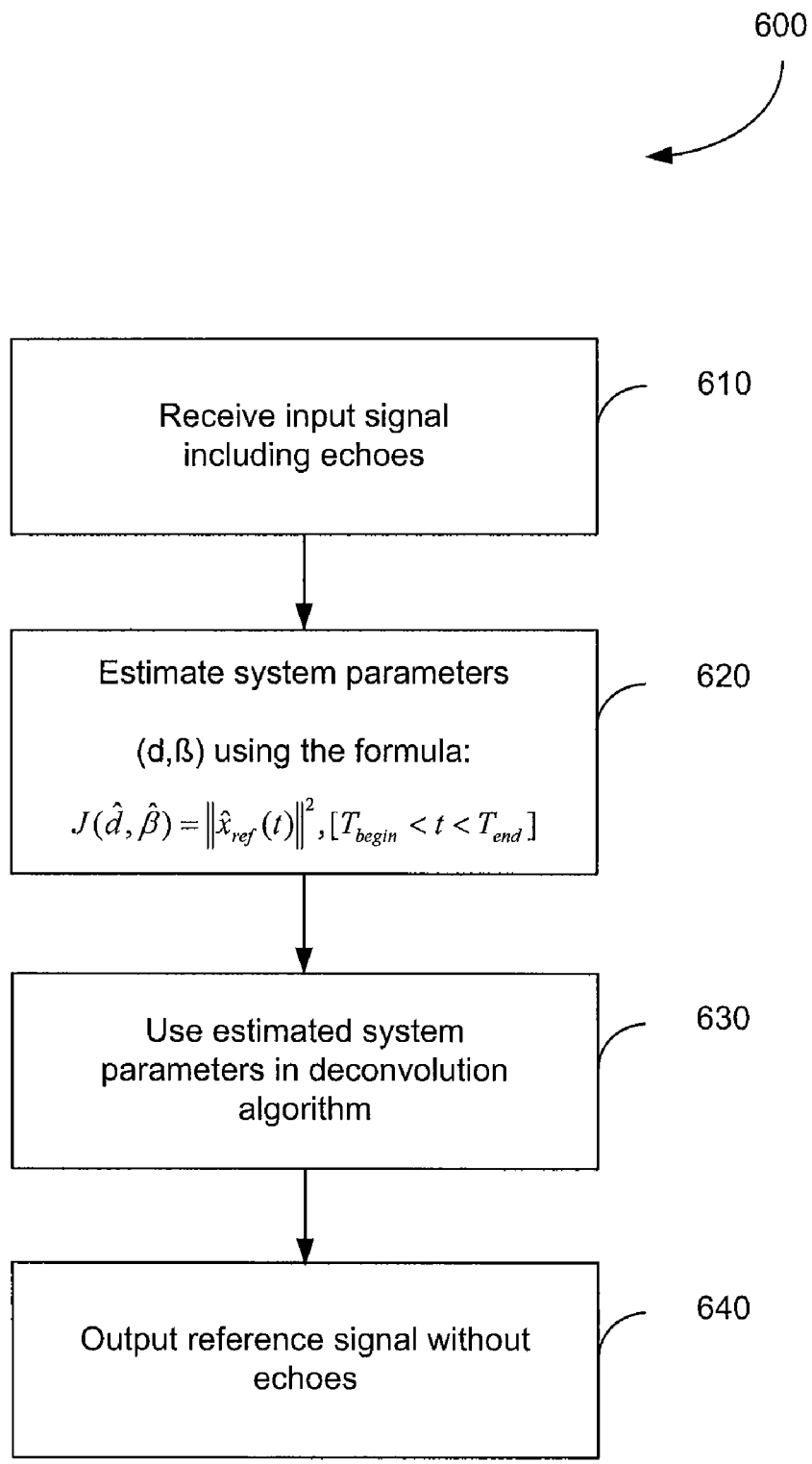
FIG. 6 is a flowchart of an embodiment of an analytical blind echo cancellation method.

Now referring to FIG. 6, shown is a flowchart of an embodiment of an analytical blind echo cancellation method 600. This method may be used to process signals received from a terahertz detector, such as that shown in FIG. 1. In step 610, an input signal is received that includes echoes. The input signal may be reconstructed from the received signals at the terahertz detector to obtain a time domain representation of the electric current at the detector.

Next, in step 620, a slab model may be used to represent the system impulse response as described above. The system parameters $\hat{d}$ and $\hat{\beta}$ may be estimated by minimizing the cost function $J(\hat{d}, \hat{\beta})=\|\hat{x}_{ref}(t)\|^2$, $[T_{begin}<t<T_{end}]$. After the system parameters have been estimated, the parameters may be used in the inverse system impulse response function to recover the reference signal in step 630. Finally, in step 640, the reference signal may be output without echoes.

Figure 7:
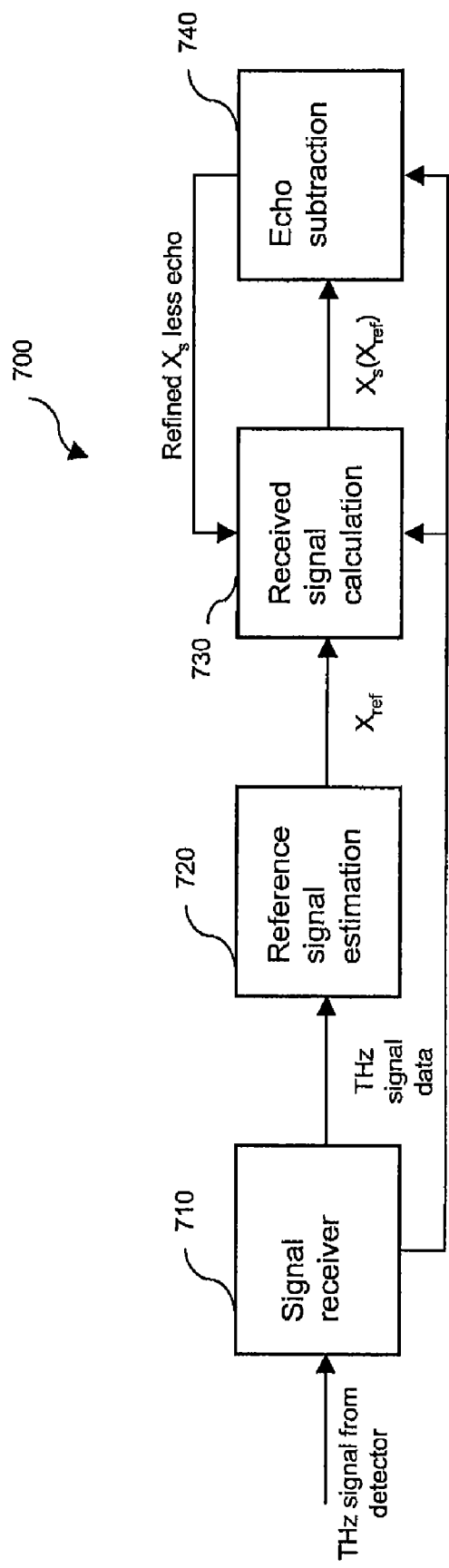
FIG. 7 is a system diagram of an embodiment of an a terahertz echo cancellation system.

Now referring to FIG. 7, shown is a system diagram of a system 700 for canceling echoes in a received terahertz signal. The system may process the received signal using a successive blind echo cancellation approach. While the system 700 is shown as a number of discrete blocks, each block may be implemented in combination with the other blocks and each block may be implemented in either software or hardware. The software may be executed on a computer, a digital signal processor or in a signal processing software suite. The system may also be implemented in hardware using a specially programmed microprocessor, a digital signal processor or a custom configured integrated circuit or FPGA.

The signal receiver 710 may be connected to a terahertz signal detector, such as the terahertz detector 130 shown in FIG. 1, or may be connected to an analog-to-digital converter that is connected to a terahertz signal detector. The function of the signal receiver 710 is to construct a time-domain digital representation of the terahertz signal from the energy received from the terahertz detector, either directly or indirectly. The time-domain terahertz signal data is then ready to be processed by the reference signal estimation block 720.

The function of the reference signal estimation block 720 is to make a first approximation of the reference signal. This may be accomplished using auto-correlation with the received signal to estimate the reference signal and the spaced echoes. Other approaches could iteratively estimate the reference signal and attempt to minimize the error, as measured by the difference in energy, between the estimate and the received terahertz signal. The estimate of the reference signal, shown as $X_{ref}$ in FIG. 7, is then passed to the received signal calculation block 730 that then represents the received signal as a function of the reference signal. This is shown as $X_s(X_{ref})$ in FIG. 7.

Next, the echo subtraction block 740 will subtract a selected echo, defined in terms of the estimated reference signal, from the received terahertz signal. The refined signal, shown as $X_s$ less echo in FIG. 7, is then used by the reference signal estimation block to re-calculate a more refined estimate of the reference signal. This refined reference signal is then used by the received signal calculation block to obtain a better estimate of the received signal as a function of the refined reference signal. The echo subtraction block 720 may again subtract a selected echo this time from the refined signal $X_s$ previously calculated by the subtraction block 720. The subtraction block 720 may also contain logic to determine when the terahertz signal processing is complete. This may be accomplished using any number of thresholds, as discussed above.

The present invention has been described here by way of example only. Various modification and variations may be made to these exemplary embodiments without departing from the spirit and scope of the invention, which is limited only by the appended claims.

The invention claimed is:

1. A method for canceling echoes in a terahertz signal, the method comprising the steps of:
   receiving a terahertz signal containing echoes;
   estimating a reference signal from the received signal;
   calculating the echoes as a function of the reference signal;
   for at least one of the successive echoes,
     subtracting the calculated echo from the received signal to form a refined reference signal; and
     re-calculating the echoes as a function of the refined reference signal.

2. The method of claim 1 wherein the steps of calculating the echoes and re-calculating the echoes comprises:
   estimating the time-shift and amplitude of each echo as a function of the corresponding reference signal.

3. The method of claim 2 wherein the steps of subtracting the calculated echo and re-calculating the echoes is repeated until a threshold is reached.

4. The method of claim 3 wherein the threshold is defined by the refined reference signal being recovered over a defined portion of echo period.

5. The method of claim 3 wherein the threshold is defined by the number of iterations performed.

6. The method of claim 3 wherein the threshold is defined by difference between refined reference signal and the prior calculation of the refined reference signal.

7. The method of claim 2 wherein the step of estimating the reference signal uses cross-correlation of the received signal.

8. The method of claim 2 wherein the received signal is expressed as a sum of scaled, time-shifted reference signals.

9. A method for canceling echoes in a terahertz signal, the method comprising the steps of:
receiving a terahertz signal containing echoes;
calculating a reference signal as a function of the received signal; and
estimating system parameters of a reflection mechanism by minimizing the energy of the calculated reference signal; and
deconvolving the received signal with an inverse transfer function using the system parameters to remove at least one of the echoes.

10. The method of claim 9 wherein the function of the reference signal is modeled as a function of the received signal:

$$\hat{x}_{ref}(t) = X_{in} - \beta X_{in}(t-2d)$$

where $\beta$ is a system parameter representing the gain and d is a system parameter representing the time-shift.

11. The method of claim 9 wherein the inverse transfer function is based on a transfer function model of a single slab medium in a vacuum.

12. The method of claim 11 wherein the transfer function is:

$$h_S(Z) = \frac{\alpha Z^{-d}}{1 - \beta Z^{-2d}} \text{ where}$$

$$\alpha = \frac{4n}{(n+1)^2}, \beta = \left(\frac{n-1}{n+1}\right)^2, \text{ and } d = \frac{nL}{C} f_{samp}$$

where n is the refractive index, L is the thickness of the slab and $f_{samp}$ is the sampling frequency.

13. A system for canceling echoes in a terahertz signal, the system comprising:
a terahertz signal receiver for receiving a terahertz signal containing echoes;
an estimator for estimating a reference signal from the received signal;
an echo subtracter for subtracting an echo from the received signal to form a refined reference signal; and
a signal calculator for calculating the echoes as a function of the reference signal, and for calculating the echoes as a function of the refined reference signal.

14. The system of claim 13 wherein the signal calculator estimates the time-shift and amplitude of each echo as a function of corresponding reference signal.

15. The system of claim 14 wherein the echo subtracter and signal calculator repeatedly subtract an echo and calculate the echoes as a function of the refined reference signal until a threshold is reached.

16. The system of claim 14 wherein the estimator uses cross-correlation of the received terahertz signal.

17. The system of claim 14 wherein the signal calculator expresses the received signal as a sum of scaled, time-shifted reference signals.

* * * * *